United States Patent [19]

Takao

[11] Patent Number: 4,540,708
[45] Date of Patent: Sep. 10, 1985

[54] SULFENYL CARBAMATE DERIVATIVES AND INSECTICIDAL COMPOSITIONS CONTAINING THE SAME

[75] Inventor: Hisashi Takao, Tokushima, Japan

[73] Assignee: Otsuka Kagaku Yakuhin Kabushiki Kaisha, Osaka, Japan

[21] Appl. No.: 548,127

[22] Filed: Nov. 2, 1983

[30] Foreign Application Priority Data

Nov. 11, 1982 [JP] Japan .................. 57-198412

[51] Int. Cl.$^3$ .................. A01N 47/24; C07D 307/86
[52] U.S. Cl. .................. 514/469; 514/477; 549/470; 260/453.3
[58] Field of Search .................. 549/470; 260/453.3; 424/285, 304, 309, 311

[56] References Cited

U.S. PATENT DOCUMENTS 4,421,693 12/1983 Goto et al. .................. 260/464
4,444,786 4/1984 Goto et al. .................. 260/453.3

*Primary Examiner*—Henry R. Jiles
*Assistant Examiner*—Bernard I. Dentz
*Attorney, Agent, or Firm*—Armstrong, Nikaido, Marmelstein & Kubovcik

[57] ABSTRACT

A sulfenyl carbamate derivative represented by the formula

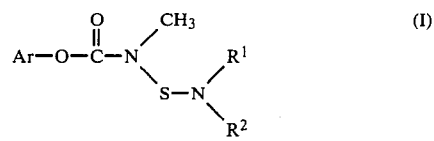

wherein Ar represents

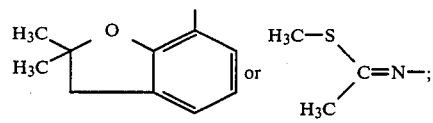

$R^1$ represents —X—COO—$R^3$ or —Y—CN in which X and Y is each an alkylene group having 1 to 6 carbon atoms and $R^3$ is an alkyl group having 1 to 8 carbon atoms; $R^2$ represents $-(CH_2)_n-O-R^4$ in which $R^4$ is an alkyl group having 1 to 5 carbon atoms, a cycloalkyl group having 3 to 6 carbon atoms, a phenyl group or a benzyl group; and n is an integer or 2 to 5.

4 Claims, No Drawings

SULFENYL CARBAMATE DERIVATIVES AND INSECTICIDAL COMPOSITIONS CONTAINING THE SAME

This invention relates to sulfenyl carbamate derivatives, a process for preparing the derivatives and insecticidal compositions containing the same.

The sulfenyl carbamate derivatives of the present invention are novel compounds represented by the formula

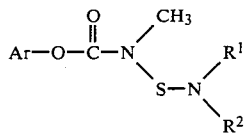

wherein Ar represents

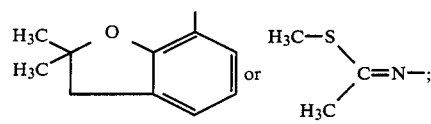

$R^1$ represents —X—COO—$R^3$ or —Y—CN in which X and Y are each an alkylene group having 1 to 6 carbon atoms and $R^3$ is an alkyl group having 1 to 8 carbon atoms; $R^2$ represents —($CH_2$)$_n$—O-$R^4$ in which $R^4$ is an alkyl group having 1 to 5 carbon atoms, a cycloalkyl group having 3 to 6 carbon atoms, a phenyl group or a benzyl group; and n is an integer of 2 to 5.

The compounds of the formula (I) have excellent insecticidal actions but are extremely low in toxicity to warm-blooded animals, hence very suitable as insecticides.

Examples of $C_{1-6}$ alkylene groups represented by X and Y in the formula (I) of the present invention are methylene, ethylene, trimethylene tetramethylene, pentamethylene, hexamethylene, etc. Examples of the group $R^3$ are $C_{1-8}$ alkyl groups such as methyl, ethyl, propyl, butyl, pentyl, hexyl, octyl, etc. Examples of $C_{1-5}$ alkyl groups represented by $R^4$ are methyl, ethyl, propyl, butyl, pentyl, etc. Examples of $C_{3-6}$ cycloalkyl groups represented by $R^4$ are cyclopentyl, etc. Examples of phenyl and benzyl groups represented by $R^4$ include those having substituents as well as those having no substituent. Examples of useful substituents are halogens such as fluorine, chlorine, bromine, iodine, lower alkyl having 1 to 4 carbon atoms, lower alkoxy having 1 to 4 carbon atoms. etc. The position of substitution is not particularly limited and 1 to 3 groups maybe substituted.

Examples of the present derivatives of the formula (I) are:

2,3-Dihydro-2,2-dimethylbenzofuran-7-yl N-(N-methoxyethyl-N-ethoxycarbonylmethylaminosulfenyl)N-methylcarbamate;
2,3-Dihydro-2,2-dimethylbenzofuran-7-yl N-(N-methoxyethyl-N-ethoxycarbonylethylaminosulfenyl)N-methylcarbamate;
2,3-Dihydro-2,2-dimethylbenzofuran-7-yl N-(N-butoxyethyl-N-ethoxycarbonylethylaminosulfenyl)N-methylcarbamate;
2,3-Dihydro-2,2-dimethylbenzofuran-7-yl N-(N-methoxypropyl-N-ethoxycarbonylethylaminosulfenyl)N-methylcarbamate;
2,3-Dihydro-2,2-dimethylbenzofuran-7-yl N-(N-phenoxyethyl-N-ethoxycarbonylethylaminosulfenyl)N-methylcarbamate:
2,3-Dihydro-2,2-dimethylbenzofuran-7-yl N-(N-benzyloxyethyl-N-ethoxycarbonylethylaminousulfenyl)N-methylcarbamate;
S-methyl N-[{N-methyl-N-(N-methoxyethyl-N-ethoxycarbonylmethylaminosulfenyl)carbamoyl}oxy]thioacetimidate;
S-methyl N-[{N-methyl-N-(N-methoxyethyl-N-ethoxycarbonylethylaminosulfenyl)carbamoyl}oxy]thioacetimidate;
S-methyl N-[{N-methyl-N-(N-butoxyethyl-N-ethoxycarbonylethylaminosulfenyl)carbamoyl}oxy]thioacetimidate;
S-methyl N-[{N-methyl-N-(methoxypropyl-N-ethoxycarbonylethylaminosulfenyl)carbamoyl]thioacetimidate;
S-methyl N-[{N-methyl-N-(N-phenoxyethyl-N-ethoxycarbonylethylaminosulfenyl)carbamoyl}oxy]thioacetimidate;
S-methyl N-[{N-methyl-N-benzyloxyethyl-N-ethoxycarbonylethylaminosulfenyl)carbamoyl}oxy]thioacetimidate; etc.

The present compounds of the formula (I) can be prepared, for example, by reacting 2,3-dihydro-2,2-dimethylbenzofuran-7-yl N-methylcarbamate of the formula (II)

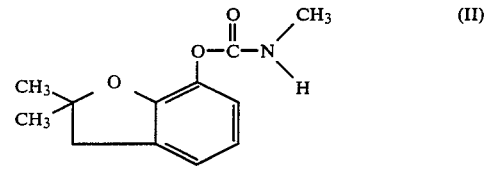

or S-methyl N-[(methylcarbamoyl)oxy]thioacetimidate of the formula (III)

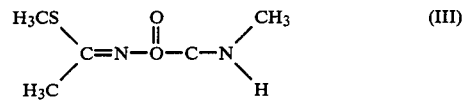

with an aminosulfenylchloride derivatives of the formula

wherein $R^1$ and $R^2$ are as defined above.

The reaction between the compound of the formula (II) or (III) and the compound of the formula (IV) is conducted in the presence or absence of a solvent suitable for this reaction.

Examples of useful solvents are methylene chloride, chloroform, carbon tetrachloride and like hydrocarbon halogenides; diethyl ether, dibutyl ether, tetrahydrofuran, dioxane and like ethers; etc. The amounts of the compounds of the formula (II) or (III) and the formula (IV) to be used are not particularly limited and can be suitably determined over a wide range. The compound of the formula (IV) is used in an amount of usually about 1 to about 1.5 moles, preferably 1 to 1.1 moles, per mole of the former. It is preferred to carry out the reaction between the compound of the formula (II) or (III) and the compound of the formula (IV) in the presence of a basic compounds. Examples of basic compounds useful in this reaction are those which can capture the hydrogen chloride to be produced by the reaction as a by-product, such as triethylamine, tributylamine, dimetylaniline, ethylmorpholine and like tertiary amines; pyridine, picoline, lutidine and like pyridines; etc. The basic compound is used in an amount sufficient to capture the hydrogen chloride to be produced by the reaction as a by-product. Usually 1 to 5 moles, preferably 1 to 2 moles, of the basic compound is employed per mole of the compound of the formula (II) or (III). The reaction, which proceeds with cooling, at room temperature or with heating, is conducted at a temperature of usually −70° to 70° C., preferably −10° to 30° C. The reaction time, although variable depending on the kind of the basic compound to be used, usually ranges from 1 to 30 hours.

The compounds of the formula (II) and (III) serving as one of the starting materials in the foregoing process are known compounds which can be synthesized by various processes. The compound of the formula (IV) to be used as another starting material is also a known compound. Examples of useful compounds of the formula (IV) are N-(2-methoxyethyl)-N-methoxycarbonylmethylamino sulfenyl chloride N-(2-methoxyethyl)-N-methoxycarbonylethylamino sulfenyl chloride N-(2-methoxyethyl)-N-butoxycarbonylethylamino sulfenyl chloride N-(2-ethoxyethyl)-N-methoxycarbonylethylamino sulfenyl chloride N-(2-cyclohexyloxyethyl)-N-methoxycarbonylethylamino sulfenyl chloride N-(2-benzyloxyethyl)-N-methoxycarbonylethylamino sulfenyl chloride N-(2-isopropyloxyethyl)-N-methoxycarbonylethylamino sulfenyl chloride N-(3-methoxypropyl)-N-methoxycarbonylethylamino sulfenyl chloride N-(3-phenoxypropyl)-N-methoxycarbonylethylamino sulfenyl chloride N-(4-phenoxybutyl)-N-methoxycarbonylethylamino sulfenyl chloride N-(5-phenoxypentyl)-N-methoxycarbonylethylamino sulfenyl chloride N-(2-methoxyethyl)-N-cyanomethylamino sulfenyl chloride N-(2-methoxyethyl)-N-cyanoethylamino sulfenyl chloride N-(3-isopropyloxypropyl)-N-cyanoethylamino sulfenyl chloride, etc.

The present compounds of the formula (I) are extremely low in toxicity to warm-blooded animals, although very high in insecticidal activity.

It is known that some carbamate compounds have high insecticidal activity, and they include those actually in use. However, many of such carbamate compounds have the drawback of being toxic to warm-blooded animals. Above all, 2,3-dihydro-2,2-dimethylbenzofuran-7-yl N-methyl carbamate (hereinafter referred to as carbofuran, as generally called) and S-methyl N-[(methylcarbamoyl)oxy]thioacetimide (hereinafter referred to as methomyl, as generally called) have high insecticidal activity and thus are useful as insecticides, but they cause problems in practical use due to high toxicity to warm-blooded animals. Accordingly, if it is possible to prepare carbamate compounds which are comparable to carbofuran and methomyl in insecticidal activity and yet have reduced toxicity to warm-blooded animals, the compounds should be very useful.

In recent years, various carbofuran sulfenyl compounds and methomyl sulfenyl compounds have been synthesized from this viewpoint, and the relation between their insecticidal activity and toxicity to warm-blooded animals is being investigated, with reports made on the results of investigation. For example, Belgian Pat. No. 817,517 discloses 2,3-dihydro-2,2-dimethylbenzofuran-7-yl N-(N,N-dibutylaminosulfenyl)N-methylcarbamate; German Patent DE-OS No. 2,254,359 2,3-dihydro-2,2-dimethylbenzofuran-7-yl N-(N-methyl-N-benzenesulfonylaminosulfenyl)N-methylcarbamate; Belgian Pat. No. 848,912 N,N'-bis-[1-metylthioacetaldehyde O-(N-methylcarbamoyl)-oxyimino]-sulfide; and Japanese Unexamined Patent Publication No. 76,835/1974 S-methyl N-[{N-methyl-N-(N-methyl-N-benzenesulfonylaminosulfenyl)carbamoyl}oxy]thioacetamidate. However, these carbofuran sulfenyl compounds and methomyl sulfenyl compounds nevertheless fail to fully fulfill the requirements in respect of insecticidal activity and toxicity to warm-blooded animals and to fish.

The present compounds of the formula (I) which are carbamate-type compounds are considerably less toxic to warm-blooded animals and to fish than known carbamate-type compounds and are comparable to or higher than known carbamate-type compounds in insecticidal activity.

The present compounds of the formula (I) have outstanding insecticidal activity or controlling effect on mites, eelworms and other agricultural and forestry noxious insects and household noxious insects, such as Hemiptera, Lepidoptera, Coleoptera, Diptera, Thysanoptera, Orthoptera, etc. The compounds are comparable or superior in such effect to carbofuran and methomyl which are thought to have the highest insecticidal activity heretofore known. Further, the toxicity of the compounds of the formula (I) to warm-blooded animals is as low as about 1/5 to about 1/50 the toxicity of carbofuran and methomyl. The present compounds exhibit insecticidal activity or controlling effect on the above-mentioned organisms in any stage or a specific stage of their growth and are therefore effectively usable for controlling them in the fields of agriculture, forestry and sanitation. The present compounds of the formula (I) are very easy to prepare with high purities in high yields and have great economical advantages.

The compounds (I) of this invention can be formulated into emulsions, wettable powders, suspensions, concentrated suspensions, granules, fine particles, pellets, dusts, coating compositions, foam sprays, aerosols, microcapsule compositions, impregnants to be applied to natural or synthetic materials, fumigants, concentrated preparations to be applied in small amounts, etc.

Various surfactants are usable for the preparations of such emulsions, dispersions, suspensions and foams. Examples of useful nonionic surfactants are polyoxyethylene alkyl phenol ethers, polyoxyethylene alkyl ethers, polyoxyethylene alkyl esters, polyoxyethylene sorbitan alkyl esters, sorbitan alkyl esters, etc. Examples of useful anionic surfactants are alkylbenzenesulfonates, alkyl sulfosuccinates, alkyl sulfates, polyoxyethylene alkylether sulfates, alkylnaphthalene sulfonates, lignin sulfonates, etc.

Solvents, diluting agents and carriers for the present compounds include various organic solvents, aerosol propellants, natural minerals, vegetables, synthetic compounds, adhesives, etc. Examples of preferred organic solvents are benzene, toluene, xylene, ethylbenzene, chlorobenzene, alkylnaphthalenes, dichloromethane, chloroethylene, cyclohexane, cyclohexanone, acetone, methyl ethyl ketone, methyl isobutyl ketone, alcohols, dimethylformamide, dimethyl sulfoxide, acetonitrile, fractions of mineral oils, etc. Examples of useful aerosol propellants are propane, butane, hydrocarbon halides, nitrogen, carbon dioxide, etc. Examples of useful natural minerals are kaolin, talc, bentonite, diatomaceous earth, clay, montmorillonite, chalk, calcite, pumice, sepiolite, dolomite, etc. Examples of useful vegetables are coconut shells, tobacco stalks, sawdust, etc. Exemplary of useful synthetic compounds are alumina, silicates, sugar polymers, etc. Also useful are adhesives, such as carboxymethyl cellulose, gum arabic, polyvinyl alcohol, polyvinyl acetate, etc. The preparations can be colored with organic or inorganic dyes.

The compounds (I) of this invention are formulated into various preparations, such as those exemplified above, so that the preparations contain, as an active ingredient, an insecticidally, miticidally or nematocidally effective amount (e.g., about 0.1 to aboug 95% by weight, preferably about 0.5 to about 90% by weight) of the compound. Depending on the application contemplated, such preparations are used as such, or as diluted with a carrier or water.

The present invention will be described below in greater detail with reference to the following examples.

EXAMPLE 1

Preparation of 2,3-dihydro-2,2-dimethylbenzofuran-7-yl N-[N-(3-methoxypropyl)-N-methoxycarbonylethylaminosulfenyl]N-methyl carbamate A 19.9 g (0.09 mole) quantity of 2,3-dihydro-2,2-dimethyl-benzofuran-7-yl-N-methyl carbamate was poured into 100 ml of a dichloroethane solution containing 24.15 g (0.1 mole) of N-(3-methoxypropyl)-N-methoxycarbonylethylaminosulfenyl-chloride. The mixture was agitated by a stirrer and 18 g (0.18 mole) of triethylamine was added dropwise thereto at less than 10° C. After the addition, the mixture was agitated at the same temperature for 2 hours. A 5% aqueous solution of sulfuric acid was added to the mixture until the pH of the mixture reached 6. The dichloroethane solution was washed with a 5% aqueous solution of sodium hydrogencarbonate and with an aqueous solution of sodium chloride, dried over anhydrous magnesium sulfate and concentrated at reduced pressure, giving 37.0 g of a yellowish brown oily product in a yield of 86.8%.

A portion of the oily product was purified by silica gel column chromatography, using n-hexane/ethyl acetate (4:1) as the solvent.

NMR in CDCl$_3$: δ=1.42 ppm (s, 6H), 1.90 ppm (t, 2H), 2.67 ppm (t, 2H), 2.98 ppm (s, 2H), 3.24 ppm (s, 3H), 3.36 ppm (s, 3H), 3.1–3.6 ppm (m, 6H), 3.58 ppm (s, 3H), 6.6–7.0 ppm (m, 3H).

| Elementary Analysis | C | H | N |
|---|---|---|---|
| Found (%) | 56.14 | 7.02 | 6.32 |
| Calcd. (%) for C$_{20}$H$_{30}$N$_2$O$_6$S = 426.542 | 56.32 | 7.09 | 6.57 |

Thus, the product was confirmed to have the following formula:

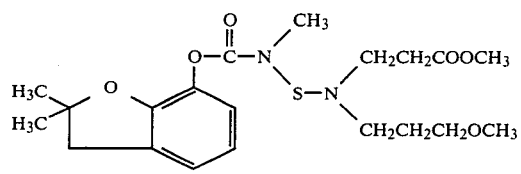

EXAMPLE 2

Preparation of 2,3-dihydro-2,2-dimethylbenzofuran-7-yl N-[N-(2-methoxyethyl)-N-cyanoethylaminosulfenyl]N-methyl-carbamate.

A 19.9 g (0.09 mole) quantity of 2,3-dihydro-2,2-dimethylbenzofuran-7-yl N-methyl-carbamate was poured into 100 ml of a dichloromethane solution containing 19.45 g (0.1 mole) of N-(2-methoxyethyl)-N-cyanoethylaminosulfenyl-chloride. The mixture was agitated by a stirrer and 18 g (0.18 mole) of triethylamine was added dropwise thereto at less than 10° C. over a period of 30 minutes. Thereafter the mixture was stirred at the same temperature for 2 hours. A 5% aqueous solution of sulfuric acid was added to the mixture until a pH of 6 was achieved. The dichloromethane solution was washed with a 5% aqueous solution of sodium hydrogencarbonate and with an aqueous solution of sodium chloride, dried over anhydrous magnesium sulfate and concentrated at reduced pressure, giving 31.8 g of a yellowish brown oily product in a yield of 84.0%.

A portion of the oily product was purified by silica gel column chromatography, using n-hexane/ethyl acetate (4:1) as the solvent.

NMR in CDCl$_3$: δ=1.42 ppm (s, 6H), 2.76 ppm (t, 2H), 2.98 ppm (s, 2H), 3.32 ppm (s, 3H), 3.38 ppm (s, 3H), 3.2–3.7 ppm (m, 6H), 6.6–7.0 ppm (m, 3H).

| Elementary Analysis | C | H | N |
|---|---|---|---|
| Found (%) | 57.02 | 6.62 | 11.15 |
| Calcd. (%) for C$_{18}$H$_{25}$N$_3$O$_4$S = 379.488 | 56.97 | 6.64 | 11.07 |

Thus, the product was confirmed to have the following formula:

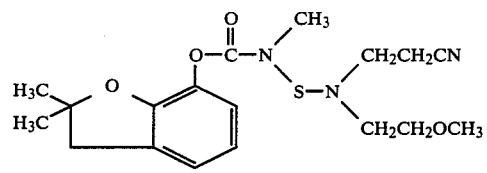

EXAMPLE 3

Preparation of S-methyl N-[{N-methyl-N-(N-methoxyethyl-N-methoxycarbonylethylaminosulfenyl)-carbamoyl}oxy]-thioacetimidate A 14.6 g (0.09 mole) quantity of S-methyl N-[(methylcarbamoyl)oxy]thioacetimidate was poured into 100 ml of a dichloroethane solution containing 22.75 g (0.1 mole) of N-methoxyethyl-N-methoxycarbonylethylaminosulfenyl-chloride. The mixture was agitated by a stirred and 18 g (0.18 mole) of triethylamine was added dropwise at less than 5° C. over a period of 30 minutes. Thereafter the mixture was agitated at the same temperature for 1 hour. A 5% aqueous solution of sulfuric acid was added to the mixture until a pH of 6 was achieved. The dichloroethane solution was washed with a 5% aqueous solution of sodium hydrogencarbonate and with an aqueous solution of sodium chloride, dried over anhydrous magnesium sulfate and concentrated at reduced pressure, giving 31 g of a yellow brown oily product in a yield of 87.8%.

A portion of the oily product was purified by silica gel column chromatography, using n-hexane/ethyl acetate (1:1) as the solvent.

NMR in CDCl$_3$: δ=2.26 ppm (s, 3H), 2.34 ppm (s, 3H), 2.66 ppm (t, 2H), 3.24 ppm (s, 3H), 3.26 ppm (s, 3H), 3.2–3.6 ppm (m, 6H), 3.56 ppm (s, 3H).

| Elementary Analysis | C | H | N |
|---|---|---|---|
| Found (%) | 40.59 | 6.54 | 11.25 |
| Calcd. (%) C$_{12}$H$_{23}$N$_3$O$_5$S = 353.472 | 40.78 | 6.56 | 11.89 |

Thus, the product was confirmed to have the following formula:

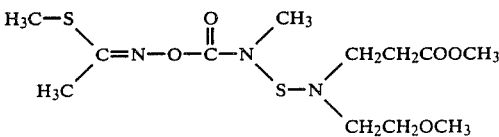

EXAMPLES 4 TO 25

The same procedure as in Examples 1 to 3 was repeated, thereby producing compounds represented by the formulae as shown in Table 1 below which also indicates the property and NMR data of each compound.

TABLE 1

| Example | Formula | Property | NMR (in CDCl$_3$) |
|---|---|---|---|
| 4 | (structure) | Oily product | 1.42(s,6H), 2.76(t, 2H), 2.98(s,2H), 3.26 (t,2H), 3.36(s,3H), 3.38(s,3H), 3.55(s, 3H), 4.10(s,2H), 6.6–7.0(m,3H) |
| 5 | (structure) | " | 1.40(s,6H), 2.78(t, 2H), 2.98(s,2H), 3.24 (t,2H), 3.36(s,3H), 3.35(s,3H), 4.13(s, 2H), 6.6–7.0(m,3H) |
| 6 | (structure) | " | 1.18(t,3H), 1.44(s, 6H), 2.76(t,2H), 2.98 (s,2H), 3.18(s,3H), 3.30(s,3H), 3.1–3.6 (m,4H), 4.02(q,2H), 4.10(s,2H), 6.6–7.0 (m,3H) |
| 7 | (structure) | " | 1.40(s,6H), 1.5–2.3 (m,2H), 2.71(t,2H), 2.98(s,2H), 3.30(s, 3H), 3.1–3.6(m,6H), 3.56(s,3H), 6.6–7.0 (m,3H), 6.97(s,5H) |
| 8 | (structure) | " | 1.12(t,3H), 1.41 (s,6H), 2.66(t,2H), 3.00(s,2H), 3.28(s, 3H), 3.1–3.8(m,6H), 3.58(s,3H), 3.5–3.9 (m,2H), 6.6–7.0(m,3H) |

TABLE 1-continued

| Example | Formula | Property | NMR (in CDCl₃) |
|---|---|---|---|
| 9 | 2,2-dimethyl-2,3-dihydrobenzofuran-7-yl O-C(=O)-N(CH₃)-S-N(CH₂CH₂COOCH₃)(CH₂CH₂OCH(CH₃)₂) | " | 1.06(d,6H), 1.42(s, 6H), 2.66(t,2H), 2.98(s,2H), 3.22(s, 3H), 3.1-3.8(m,6H), 3.56(s,3H), 3.5-3.8 (m,1H), 6.6-7.0(m, 3H) |
| 10 | 2,2-dimethyl-2,3-dihydrobenzofuran-7-yl O-C(=O)-N(CH₃)-S-N(CH₂CH₂COOCH₃)(CH₂CH₂O-cyclohexyl) | " | 0.9-1.7(m,10H), 1.40 (s,6H), 2.67(t,2H), 3.00(s,2H), 3.30(s, 3H), 3.1-3.9(m,7H), 3.58(s,2H), 6.6-7.0 (m,3H) |
| 11 | 2,2-dimethyl-2,3-dihydrobenzofuran-7-yl O-C(=O)-N(CH₃)-S-N(CH₂CH₂CN)(CH₂CH₂CH₂OCH(CH₃)₂) | " | 1.06(d,6H), 1.42(s, 6H), 1.90(t,2H), 2.67 (t,2H), 2.96(s,2H), 3.28(s,3H), 3.1-3.9 (m,7H), 6.6-7.0(m, 3H) |
| 12 | 2,2-dimethyl-2,3-dihydrobenzofuran-7-yl O-C(=O)-N(CH₃)-S-N(CH₂CH₂COOC₄H₉)(CH₂CH₂OCH₃) | " | 0.7-1.8(m,7H), 1.43 (s,6H), 2.68(t,2H), 3.00(s,2H), 3.25(s, 3H), 3.32(s,3H), 3.1-4.1(m,6H), 4.05(q, 2H), 6.6-7.0(m,3H) |
| 13 | 2,2-dimethyl-2,3-dihydrobenzofuran-7-yl O-C(=O)-N(CH₃)-S-N(CH₂CH₂COOCH₃)(CH₂CH₂OCH₂-phenyl) | " | 1.42(s,6H), 2.66(t, 2H), 2.98(s,2H), 3.22 (s,3H), 3.1-3.7(m, 6H), 3.56(s,3H), 4.3-4.7(m,2H), 6.6-7.0(m, 3H), 7.12(s,5H) |
| 14 | 2,2-dimethyl-2,3-dihydrobenzofuran-7-yl O-C(=O)-N(CH₃)-S-N(CH₂CH₂COOCH₃)(CH₂CH₂CH₂CH₂O-phenyl) | " | 1.43(s,6H), 1.5-2.1 (m,4H), 2.70(t,2H), 3.00(s,2H), 3.30(s, 3H), 3.1-3.7(m,6H), 3.60(s,3H), 6.6-7.0 (m,3H), 6.96(s,5H) |
| 15 | 2,2-dimethyl-2,3-dihydrobenzofuran-7-yl O-C(=O)-N(CH₃)-S-N(CH₂CH₂COOCH₃)(CH₂CH₂CH₂CH₂CH₂O-phenyl) | " | 1.42(s,6H), 1.0-2.2 (m,6H), 2.70(t,2H), 2.98(s,2H), 3.24(s, 2H), 3.1-3.7(m,6H), 3.60(s,3H), 6.6-7.0 (m,3H), 6.94(s,5H) |
| 16 | (H₃C-S)(H₃C)C=N-O-C(=O)-N(CH₃)-S-N(CH₂CH₂COOCH₃)(CH₂CH₂CH₂OCH₃) | " | 1.84(t,2H), 2.22(s, 3H), 2.32(s,3H), 2.66 (t,2H), 3.22(s,3H), 3.30(s,3H), 3.0-3.6 (m,6H), 3.60(s,3H) |
| 17 | (H₃C-S)(H₃C)C=N-O-C(=O)-N(CH₃)-S-N(CH₂CH₂CN)(CH₂CH₂OCH₃) | " | 2.23(s,3H), 2.32(s, 3H), 2.68(t,2H), 3.23 (s,3H), 3.30(s,3H), 3.1-3.6(m,6H) |

TABLE 1-continued

| Example | Formula | Property | NMR (in CDCl₃) |
|---|---|---|---|
| 18 | H₃C—S\C=N—O—C(=O)—N(CH₃)—C(=N—CH₂CH₂OCH₃)—CH₂CN / H₃C | " | 2.22(s,3H), 2.32(s,3H), 2.68(t,2H), 3.22(s,3H), 3.26(t,2H), 3.30(s,3H), 4.10(s,2H) |
| 19 | H₃C—S\C=N—O—C(=O)—N(CH₃)—S—N(CH₂COOC₂H₅)(CH₂CH₂OCH₃) / H₃C | " | 1.18(t,3H), 2.23(s,3H), 2.32(s,3H), 2.66(t,2H), 3.22(s,3H), 3.26(t,2H), 3.30(s,3H), 4.10(s,2H), 4.16(q,2H) |
| 20 | H₃C—S\C=N—O—C(=O)—N(CH₃)—S—N(CH₂CH₂COOCH₃)(CH₂CH₂CH₂O—Ph) / H₃C | " | 1.78(t,2H), 2.22(s,3H), 2.33(s,3H), 2.64(t,2H), 3.22(s,3H), 2.9–3.5(m,6H), 3.58(s,3H), 6.98(s,5H) |
| 21 | H₃C—S\C=N—O—C(=O)—N(CH₃)—S—N(CH₂CH₂COOCH₃)(CH₂CH₂OCH(CH₃)₂) / H₃C | " | 1.06(d,6H), 2.26(s,3H), 2.36(s,3H), 2.70(t,2H), 3.1–4.0(m,7H), 3.22(s,3H), 3.60(s,3H) |
| 22 | H₃C—S\C=N—O—C(=O)—N(CH₃)—S—N(CH₂CH₂COOCH₃)(CH₂CH₂O—cyclohexyl) / H₃C | " | 0.9–1.7(m,10H), 2.26(s,3H), 2.36(s,3H), 2.66(t,2H), 3.22(s,3H), 3.1–3.9(m,7H), 3.60(s,3H) |
| 23 | H₃C—S\C=N—O—C(=O)—N(CH₃)—S—N(CH₂CH₂CN)(CH₂CH₂CH₂OCH(CH₃)₂) / H₃C | " | 1.06(d,6H), 1.90(t,2H), 2.26(s,3H), 2.36(s,3H), 2.67(t,2H), 3.22(s,3H), 3.1–4.0(m,7H) |
| 24 | H₃C—S\C=N—O—C(=O)—N(CH₃)—S—N(CH₂CH₂COOC₄H₉)(CH₂CH₂OCH₃) / H₃C | " | 0.7–1.8(m,7H), 2.26(s,3H), 2.38(s,3H), 2.66(t,2H), 3.20(s,3H), 3.2–4.2(m,6H), 3.60(s,3H), 4.10(q,2H) |
| 25 | H₃C—S\C=N—OC(=O)—N(CH₃)—S—N(CH₂CH₂COOCH₃)(CH₂CH₂CH₂CH₂O—Ph) / H₃C | " | 1.5–2.1(m,4H), 2.25(s,3H), 2.38(s,3H), 3.21(s,3H), 3.1–3.8(m,8H), 3.60(s,3H), 6.98(s,5H) |

Preparation Examples of this invention are given below.

There prescriptions are applicable to all the compounds of this invention; a suitable prescription is usable for a particular application. The prescriptions are shown only for illustrative purposes, and the proportions of the active component, organic solvent, surfactant, carrier, etc., can also be changed. The percentages are all by weight.

PREPARATION EXAMPLE 1

Wettable powder

Compound of Example 1: 50.0%

Kaolin: 30.0%
Talc: 10.0%
Emal 40 powder: 5.5%
Demol EP powder: 3.5%
Alkyl phosphate: 1.0%

PREPARATION EXAMPLE 2

Emulsion

Compound of Example 16: 50.0%
Xylene: 30.0%
Cyclohexanone: 10.0%
Tween 80: 6.5%
Span 80: 3.5%

PREPARATION EXAMPLE 3

Granule

Wettable powder of Preparation Example 1: 40.0%
Dolomite: 60.0%

Wettable powder was prepared by uniformly mixing the ingredients and finely pulverizing the mixture and an emulsion was prepared by uniformly mixing the ingredients and dissolving the mixture. Granules were prepared by uniformly mixing the ingredients, adding 15 parts by weight of a 2% aqueous solution of carboxymethyl cellulose per 100 parts by weight of the mixture, thoroughly kneading the resulting mixture, and granulating the same by using a granulator. The thus-granulated product was finely cleaved and dried to obtain the desired granule.

Test Examples are given below.

TEST EXAMPLE 1

Ten third-instar larvae of tobacco cutworm (*Spodoptera litura*) were placed on a cabbage (one-month-old seedling) planted in a pot, and a 50% emulsion of the compound to be tested was diluted to a specified concentration and applied to the leaves of the plant to fully wet them. The test compound of each specified concentration was tested on two pots. Three days later, the larvae were checked for mortality, with the result listed in Table 2, which also shows the results achieved for control groups and untreated groups for comparison.

TABLE 2

| Compound | Mortality (%) Concentration of Active Ingredient (ppm) | | | |
|---|---|---|---|---|
| (Example No.) | 1000 | 500 | 250 | 125 |
| 1 | 90 | 80 | 65 | 40 |
| 2 | 85 | 70 | 55 | 40 |
| 3 | 90 | 85 | 70 | 55 |
| 4 | 90 | 80 | 65 | 45 |
| 5 | 90 | 80 | 70 | 50 |
| 6 | 90 | 80 | 70 | 55 |
| 7 | 85 | 75 | 60 | 40 |
| 8 | 90 | 80 | 60 | 40 |
| 9 | 90 | 80 | 60 | 40 |
| 10 | 85 | 70 | 50 | 35 |
| 11 | 80 | 70 | 50 | 35 |
| 12 | 85 | 75 | 55 | 40 |
| 13 | 85 | 70 | 55 | 40 |
| 14 | 80 | 70 | 50 | 35 |
| 15 | 80 | 70 | 50 | 40 |
| 16 | 100 | 100 | 100 | 100 |
| 17 | 100 | 100 | 95 | 85 |
| 18 | 100 | 100 | 100 | 100 |
| 19 | 100 | 100 | 100 | 90 |
| 20 | 100 | 100 | 95 | 90 |
| 21 | 100 | 100 | 100 | 100 |
| 22 | 100 | 100 | 100 | 90 |
| 23 | 100 | 100 | 95 | 85 |
| 24 | 100 | 100 | 95 | 80 |
| 25 | 100 | 100 | 90 | 80 |

TABLE 2-continued

| Compound | Mortality (%) Concentration of Active Ingredient (ppm) | | | |
|---|---|---|---|---|
| (Example No.) | 1000 | 500 | 250 | 125 |
| Control* | 100 | 100 | 90 | 85 |
| Untreated area | | 0 | | |

*Control: S—methyl N—[(methylcarbamoyl)oxy]thioacetimidate

TEST EXAMPLE 2

An emulsion of specified concentration was prepared from a 50% wettable powder of the compound to be tested and applied to the leaves of paddy rice (one-month-old seedlings) planted in a pot to fully wet the leaves. After the emulsion had been dried, the pot was covered with a net cage, into which 10 female adults of green rice leafhopper (*Nephotettix cincticeps*) were released. The compound of each specified concentration was tested on two pots. Three days later, the insects were checked for mortality, with the result listed in Table 3, which also shows the results achieved for control groups and untreated groups for comparison.

TABLE 3

| Test compound | Mortality (%) Concentration of Active Ingredient (ppm) | | |
|---|---|---|---|
| (Example No.) | 800 | 400 | 200 |
| 1 | 100 | 90 | 70 |
| 2 | 100 | 85 | 65 |
| 3 | 100 | 90 | 65 |
| 4 | 100 | 95 | 75 |
| 5 | 100 | 90 | 70 |
| 6 | 100 | 95 | 70 |
| 7 | 100 | 80 | 60 |
| 8 | 100 | 90 | 75 |
| 9 | 100 | 90 | 75 |
| 10 | 100 | 85 | 65 |
| 11 | 100 | 90 | 70 |
| 12 | 100 | 85 | 70 |
| 13 | 100 | 85 | 65 |
| 14 | 100 | 85 | 65 |
| 15 | 100 | 80 | 65 |
| 16 | 100 | 100 | 90 |
| 17 | 100 | 95 | 80 |
| 18 | 100 | 95 | 80 |
| 19 | 100 | 100 | 90 |
| 20 | 100 | 90 | 80 |
| 21 | 100 | 100 | 85 |
| 22 | 100 | 95 | 80 |
| 23 | 100 | 95 | 80 |
| 24 | 100 | 95 | 85 |
| 25 | 100 | 90 | 85 |
| Control* | 100 | 100 | 90 |
| Untreated area | | 0 | |

*Control: S—methyl-N—[(methylcarbamoyl)oxy]thioacetimidate

TEST EXAMPLE 3

Granules containing 20% of the compound to be tested were mixed, in a specified amount, with soil contaminated with larvae of southern root-knot nematode (*Meloidogyne incognita*), and tomato seedlings were immediately transplanted in the soil. One month later, the roots of the plant were checked for the formation of nodules. Two test areas, $2 \times 2$ m² each, were used for the compound as applied in each specified amount. The degree of formation of the nodules was determined according to the criteria given below, with the result shown in Table 4. For comparison, Table 4 also shows the results achieved in control areas and untreated areas.

Degree of formation of nodules:
0: 0%, 1: 1-24%, 2: 25-49%, 3: 50-74%, 4: 75-100%

TABLE 4

| Test Compound | Degree of Formation of Nodules Amount of Granules Applied (Kg/10a) | | |
|---|---|---|---|
| (Example No.) | 50 | 25 | 10 |
| 1 | 0 | 1 | 2 |
| 2 | 0 | 1 | 2 |
| 3 | 0 | 1 | 2 |
| 4 | 0 | 1 | 2 |
| 5 | 0 | 1 | 2 |
| 6 | 0 | 1 | 3 |
| 7 | 0 | 1 | 2 |
| 8 | 0 | 1 | 3 |
| 9 | 0 | 1 | 3 |
| 10 | 0 | 1 | 3 |
| 11 | 0 | 1 | 2 |
| 12 | 0 | 1 | 3 |
| 13 | 0 | 1 | 3 |
| 14 | 0 | 1 | 2 |
| 15 | 0 | 1 | 2 |
| 16 | 1 | 2 | 3 |
| 17 | 2 | 3 | 4 |
| 18 | 2 | 3 | 4 |
| 19 | 1 | 2 | 3 |
| 20 | 1 | 2 | 3 |
| 21 | 1 | 2 | 4 |
| 22 | 1 | 2 | 3 |
| 23 | 1 | 2 | 4 |
| 24 | 1 | 2 | 4 |
| 25 | 1 | 3 | 4 |
| Control* | 2 | 4 | 4 |
| Untreated area | | | 4 |

*Control: Bis(2-chloro-1-methylethyl)ether

TEST EXAMPLE 4

Compounds of this invention were tested on male mice for acute toxicity by oral administration. Table 5 shows LD$_{50}$ values determined by the Litchfield-Wilcoxon method from the mortality on the seventh day.

TABLE 5

| Test Compound (Example No.) | LD$_{50}$ (mg/g) |
|---|---|
| 1 | 110 |
| 2 | 98 |
| 3 | 105 |
| 4 | 90 |
| 5 | 68 |
| 6 | 106 |
| 7 | 118 |
| 8 | 109 |
| 9 | 115 |
| 10 | 117 |
| 11 | 105 |
| 12 | 120 |
| 13 | 125 |
| 14 | 128 |
| 15 | 135 |
| 16 | 250 |
| 17 | 170 |
| 18 | 165 |
| 19 | 180 |
| 20 | 280 |
| 21 | 260 |
| 22 | 250 |
| 23 | 200 |
| 24 | 300 |
| 25 | 310 |
| Control 1 | 5.6 |
| Control 2 | 16 |

Control 1: 2,3-dihydro-2,2-dimethylbenzofuran-7-yl-N—methylcarbamate

I claim:
1. A sulfenyl carbamate derivative represented by the formula

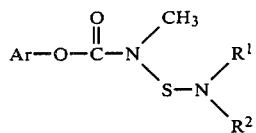

wherein Ar represents

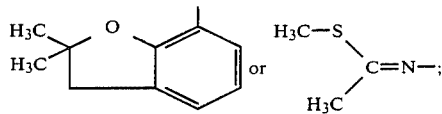

$R^1$ represents —X—COO—$R^3$ or —Y—CN in which each of X and Y is an alkylene group having 1 to 6 carbon atoms and $R^3$ is an alkyl group having 1 to 8 carbon atoms; $R^2$ represents —(CH$_2$)$_n$O—$R^4$ in which $R^4$ is an alkyl group having 1 to 5 carbon atoms, a cycloalkyl group having 3 to 6 carbon atoms, a phenyl group which is unsubstituted or substituted with 1 to 3 substituents selected from the group consisting of halogen, an alkyl group having 1 to 4 carbon atoms and an alkoxy group having 1 to 4 carbon atoms, or a benzyl group which is unsubstituted or substituted with 1 to 3 substituents selected from the group consisting of halogen, an alkyl group of 1 to 4 carbon atoms and an alkoxy group of 1 to 4 carbon atoms; and n is an integer of 2 to 5.

2. An insecticidal composition comprising an insecticidally effective amount of a sulfenyl carbamate derivative represented by the formula

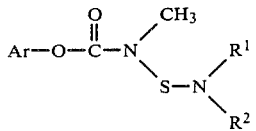

wherein Ar represents

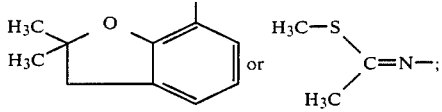

$R^1$ represents —X—COO—$R^3$ or —Y—CN in which each of X and Y is an alkylene group having 1 to 6 carbon atoms and $R^3$ is an alkyl group having 1 to 8 carbon atoms; $R^2$ represents —(CH$_2$)$_n$O—$R^4$ in which $R^4$ is an alkyl group having 1 to 5 carbon atoms, a cycloalkyl group having 3 to 6 carbon atoms, a phenyl group which is unsubstituted or substituted with 1 to 3 substituents selected from the group consisting of halogen, an alkyl group having 1 to 4 carbon atoms and an alkoxy group having 1 to 4 carbon atoms, or a benzyl group which is unsubstituted or substituted with 1 to 3 substituents selected from the group consisting of halogen, an alkyl group of 1 to 4 carbon atoms and an alkoxy group of 1 to 4 carbon atoms; and n is an integer of 2 to 5, in combination with an insecticidally acceptable solvent, diluent or carrier.

3. A miticidal composition comprising a miticidally effective amount of a sulfenyl carbamate derivative of the formula

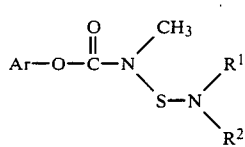

wherein Ar represents

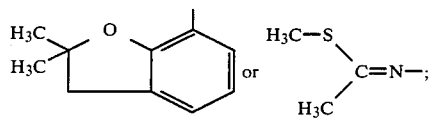

$R^1$ represents —X—COO—$R^3$ or —Y—CN in which each of X and Y is an alkylene group having 1 to 6 carbon atoms and $R^3$ is an alkyl group having 1 to 8 carbon atoms; $R^2$ represents $-(CH_2)_n-O-R^4$ in which $R^4$ is an alkyl group having 1 to 5 carbon atoms, a cycloalkyl group having 3 to 6 carbon atoms, a phenyl group which is unsubstituted or substituted with 1 to 3 substituents selected from the group consisting of halogen, an alkyl group having 1 to 4 carbon atoms and an alkoxy group having 1 to 4 carbon atoms, or a benzyl group which is unsubstituted or substituted with 1 to 3 substituents selected from the group consisting of halogen, an alkyl group of 1 to 4 carbon atoms and an alkoxy group of 1 to 4 carbon atoms; and n is an integer of 2 to 5, in combination with a miticidally acceptable solvent, diluent or carrier.

4. A nematocidal composition comprising a nematocidally effective amount of a sulfenyl carbamate derivative of the formula

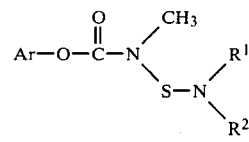

wherein Ar represents

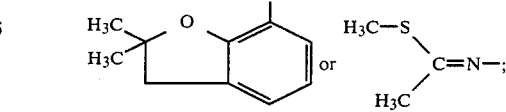

$R^1$ represents —X—COO—$R^3$ or —Y—CN in which each of X and Y is an alkylene group having 1 to 6 carbon atoms and $R^3$ is an alkyl group having 1 to 8 carbon atoms; $R^2$ represents $-(CH_2)_n-O-R^4$ in which $R^4$ is an alkyl group having 1 to 5 carbon atoms, a cycloalkyl group having 3 to 6 carbon atoms, a phenyl group which is unsubstituted or substituted with 1 to 3 substituents selected from the group consisting of halogen, an alkyl group having 1 to 4 carbon atoms and an alkoxy group having 1 to 4 carbon atoms, or a benzyl group which is unsubstituted or substituted with 1 to 3 substituents selected from the group consisting of halogen, an alkyl group of 1 to 4 carbon atoms and an alkoxy group of 1 to 4 carbon atoms; and n is an integer of 2 to 5, in combination with a nematocidally acceptable solvent, diluent or carrier.

* * * * *